US009867838B2

(12) United States Patent
Lyles et al.

(10) Patent No.: US 9,867,838 B2
(45) Date of Patent: Jan. 16, 2018

(54) METHODS FOR TREATING HEART FAILURE USING BISPHOSPHONATE COMPOSITIONS (75) Inventors: Kenneth W. Lyles, Durham, NC (US); Cathleen S. Colon-Emeric, Durham, NC (US); Christopher M. O'Connor, Durham, NC (US); Richard S. Stack, Chapel Hill, NC (US); Colleen Stack, Chapel Hill, NC (US)

(73) Assignee: DUKE UNIVERSITY, Durham, NC (US)

( * ) Notice: Subject to any disclaimer, the term of this patent is extended or adjusted under 35 U.S.C. 154(b) by 453 days.

(21) Appl. No.: 13/393,248

(22) PCT Filed: Sep. 1, 2010

(86) PCT No.: PCT/US2010/047417
§ 371 (c)(1),
(2), (4) Date: Apr. 27, 2012

(87) PCT Pub. No.: WO2011/028737
PCT Pub. Date: Mar. 10, 2011

(65) Prior Publication Data
US 2012/0208786 A1 Aug. 16, 2012

Related U.S. Application Data (60) Provisional application No. 61/238,797, filed on Sep. 1, 2009.

(51) Int. Cl.
A61K 47/00 (2006.01)
A61K 31/663 (2006.01)
A61K 31/66 (2006.01)

(52) U.S. Cl.
CPC ............ A61K 31/663 (2013.01); A61K 31/66 (2013.01)

(58) Field of Classification Search
None
See application file for complete search history.

(56) References Cited

U.S. PATENT DOCUMENTS

| | | |
|---|---|---|
| 3,962,432 A | 6/1976 | Schmidt-Dunker |
| 4,639,338 A | 1/1987 | Stahl et al. |
| 4,687,767 A | 8/1987 | Bosies et al. |
| 4,711,880 A | 12/1987 | Stahl et al. |
| 4,857,513 A | 8/1989 | Oku et al. |
| 4,927,814 A | 5/1990 | Gall et al. |
| 4,939,130 A | 7/1990 | Jaeggi et al. |
| 4,942,157 A | 7/1990 | Gall et al. |
| 4,963,536 A | 10/1990 | Oku et al. |
| 5,057,505 A | 10/1991 | Widler et al. |
| 5,157,027 A | 10/1992 | Biller et al. |
| 5,403,829 A | 4/1995 | Lehtinen et al. |
| 5,412,141 A * | 5/1995 | Nugent .......................... 558/214 |
| 5,646,134 A | 7/1997 | Yates |
| 5,733,564 A | 3/1998 | Lehtinen |
| 5,965,547 A | 10/1999 | Goodship et al. |
| 6,117,856 A | 9/2000 | Binderman et al. |
| 6,255,288 B1 | 7/2001 | Goodship et al. |
| 8,052,987 B2 | 11/2011 | Horowitz et al. |
| 2002/0187184 A1 | 12/2002 | Golomb et al. |
| 2003/0064965 A1 | 4/2003 | Richter |
| 2004/0157799 A1 * | 8/2004 | Seaman ........................ 514/89 |
| 2004/0204448 A1 * | 10/2004 | Muller et al. ................ 514/309 |
| 2004/0265391 A1 | 12/2004 | Danenberg et al. |
| 2004/0266734 A1 * | 12/2004 | Danenberg et al. ............ 514/89 |
| 2005/0026871 A1 | 2/2005 | Flashner-Barak et al. |
| 2005/0272707 A1 * | 12/2005 | Horowitz et al. ............ 514/102 |
| 2006/0051407 A1 | 3/2006 | Richter et al. |
| 2006/0069068 A1 | 3/2006 | Kajander et al. |
| 2006/0069069 A1 * | 3/2006 | Kajander ............... A61K 31/19 514/89 |
| 2006/0166937 A1 | 7/2006 | Prescott |
| 2006/0205692 A1 | 9/2006 | Montes et al. |
| 2008/0146489 A1 | 6/2008 | Pacetti et al. |
| 2008/0193564 A1 | 8/2008 | Horowitz et al. |
| 2010/0144679 A1 | 6/2010 | Lyles |
| 2011/0112053 A1 | 5/2011 | Li et al. |

FOREIGN PATENT DOCUMENTS

| | | |
|---|---|---|
| DE | 19738005 | 3/1999 |
| DE | 19738005 DE | 4/1999 |
| EP | 0600834 | 6/1994 |
| WO | WO89/09775 | 10/1989 |
| WO | WO92/03451 | 3/1992 |

(Continued)

OTHER PUBLICATIONS

M. Maurer et al., Dissociation Between Exercise Hemodynamics and Exercise Capacity in Patients With Chronic Heart Failure and Marked Increase in Ejection Fraction After Treatment With Beta-Adrenergic Receptor Antagonists, American Journal of Cardiology; vol. 91, Feb. 1, 2003.*
Yves Juilliere et al., Beneficial cumulative role of both nitroglycerin and dobutamine on right ventricular systolic function in congestive heart failure patients awaiting heart transplantation, International Journal of Cardiology, 52, 1995, pp. 17-22.*
Ganesh Chandra Jagetia et al. , Antarth, A Polyherbal Preparation Protects against the Doxorubicin-induced Toxicity without Compromising its Antineoplastic Activity, Phytotherapy Research—Phytother. Res. 19, 772-778 (2005).*
Juergens et al., Zschr. Inn. Med., Jahrg. 32 (1977) Heft. vol. 32, Issue: 3, pp. 70-73, (English Abstract); Journal; Article; 1977, ISSN: 0044-2542, Journal Code: 21730470R, Germany, East: German Democratic Republic.*
Maurer et al., American Journal of Cardiology, vol. 91, Feb. 1, 2003.*

(Continued)

Primary Examiner — Sreeni Padmanabhan
Assistant Examiner — Jeanmarie Calvillo
(74) Attorney, Agent, or Firm — Marianne Fuierer; Moore & Van Allen, PLLC (57) ABSTRACT The present invention provides for methods for treating and/or reducing cardiac dysfunction by administering to subject a therapeutically effective amount of a bisphosphonate, functional analogue or a pharmaceutically effective salt thereof.

19 Claims, 3 Drawing Sheets (56) References Cited

FOREIGN PATENT DOCUMENTS

| WO | WO9221355 | 12/1992 | | |
|---|---|---|---|---|
| WO | WO9421266 | 9/1994 | | |
| WO | WO99/38998 | 8/1999 | | |
| WO | WO01/49295 | 7/2001 | | |
| WO | WO0149295 | 7/2001 | | |
| WO | WO 01/64207 | * 9/2001 | ............ | A61K 31/00 |
| WO | WO0189494 | 11/2001 | | |
| WO | WO0197788 | 12/2001 | | |
| WO | WO2003086415 | 10/2003 | | |
| WO | WO2004024166 | 3/2004 | | |
| WO | WO2005002545 | 1/2005 | | |
| WO | WO2005027921 | 3/2005 | | |
| WO | WO06/019843 | 2/2006 | | |
| WO | WO06/019844 | 2/2006 | | |
| WO | WO2009082437 | 7/2009 | | |

OTHER PUBLICATIONS

Robbins et al., American Journal of Cardiology, vol. 91, Feb. 1, 2003, p. 360.*
Lee., P. et al (Bone Marrow Transplantation, 2008, vo. 42, p. 363-364.*
Bevilacqua, et al., Lupus (2005) 14, 773-779.*
Heart Rhythm Society, copyright 2016, online article, http://www.hrsonline.org/Patient-Resources/The-Normal-Heart/Ejection-Fraction.*
Massy et al., Clin J Am Soc Nephrol 4: 1128-1135, 2009. doi:10.2215/CJN.00260109.*
Michael S. Ewer, MD, MPH, Robert S. Benjamin, MD, and Edward T.H. Yeh, MD.Kufe DW, Pollock RE, Weichselbaum RR, et al., editors. Holland-Frei Cancer Medicine. 6th edition. Hamilton (ON): BC Decker; 2003.*
Full, et al, The inextricable link between atherosclerosis and prototypical inflammatory diseases rheumatoid arthritis and systemic lupus erythematosus, Published: Apr. 3, 2009 Arthritis Research & Therapy 2009, 11:217 This article is online at http://arthritis-research.com/content/11/2/217 © 2009 BioMed Central.*
Full, et al, The inextricable link between atherosclerosis and prototypical inflammatory diseases rheumatoid arthritis and systemic lupus erythematosus, Published: Apr. 3, 2009 Arthritis Research & Therapy 2009, 11:217 (doi:10.1186/ar2631) (Year: 2009).*
Briesacher, Becky A. et al., "Consequences of Poor Compliance with Bisphosphonates", Bone, 41 (2007) pp. 882-887.
Christiansen, C. et al., "Dose Dependent Effects on Bone Resorption and Formation of Intermittently Administered Intravenous Ibandronate", Osteoporosis International, vol. 14, (2003), pp. 609-613.
Claxton, Ami J. et al., "A Systematic Review of the Association Between Dose Regimens and Medication Compliance", Clinical Therapeutics, vol. 23, No. I, (2001), pp. 1296-1310.
Cramer J.A. et al., "A Systematic Review of Persistence and Compliance with Bisphosphonates for Osteoporosis", Osteoporos Int. (2007) 18: pp. 1023-1031.

Cramer, Joyce A. et al., "The Effect of Dosing Frequency on Compliance and Persistence with Bisphosphonate Therapy in Postmenopausal Women: A Comparison of Studies in the United States, the United Kingdom, and France", Clinical Therapeutics, vol. 28, No. 10, (2006), pp. 1686-1694.
Lyles, Kenneth W. et al. "Zoledronic Acid and Clinical Fractures and Mortality After Hip Fracture." New England Journal of Medicine, vol. 357, No. 18, Nov. 1, 2007, pp. 1799-1809.
Need, Allan G. et al. "Vitamin D Status: Effects on Parathyroid Hormone and 1,25-dihydroxyvitamin D in Postmenopausal Women." American Journal of Clinical Nutrition, vol. 71, No. 6, Jun. 2000, pp. 1577-1581.
Recker, Robert R. et al., "Effect of Dosing Frequency on Bisphosphonate Medication Adherence in a Large Longitudinal Cohort of Women", Mayo Clinic Proc. Jul. 2005, 80 (7): pp. 856-861.
Reid, David M. et al., "Zoledronic Acid and Risedronate in the Prevention and Treatment of Glucocorticoid-Induced Osteoporosis (Horizon): A Multicentre, Double-Blind, Double-Dummy, randomized Controlled Trial", Lancet, vol. 373, Apr. 11, 2009, pp. 1253-1263.
Reid, Ian R. et al. "Intravenous Zoledronic Acid in Postmenopausal Women with Low Bone Mineral Density." New England Journal of Medicine, vol. 346, No. 9, Feb. 28, 2002, pp. 653-661.
Seeman, E. et al., "Non-Compliance: The Achilles' Heel of Antifracture Efficacy", Osteoporos Int. (2007) 18: pp. 711-719.
Solomon, C.G. "Bisphosphonates and Osteoporosis." New England Journal of Medicine, Feb. 28, 2002, US, vol. 346, No. 9, p. 642.
Thiebaud, D. et al., "Three Monthly Intravenous Injections of Ibandronate in the Treatment of Postmenopausal Osteoporosis", The American Journal of Medicine, vol. 103, Oct. 1997, pp. 298-307.
Wu, L. et al. *Zoledronate inhibits the proliferation, adhesion, and migration of vascular smooth muscle cells*. Eur. J. Pharm. 602 (2009), 124-131.
Shioi, A. *Atherosclerosis and Bisphosphonate*. Clinical Calcium 13 (2003), 169. (Abstract Only).
Ono, K. *Regulation of Calcification by Bisphosphonates*. Clinical Calcium 14 (2004), 906. (Abstract only.
Fiore, C. et al. *Bisphosphonates and Atherosclerosis*. J. Endocrinol. Invest. 32 (2009), 38.
Crouch, S. *The In Vitro Effect of BM.21.0955 (Ibandronate) on Monocyte Production of Inflammatory Cytokines*. Blood 88 (1996), Suppl. 1, p. 158A.
Tintut, Y. et al. *Recent advances in multifactorial regulation of vascular calcification*. Current Opinion in Lipidology 12 (2001), 555-560.
Tuominen, O. et al. Suppression of Viability and Acetyl-LDL Metabolism in Raw 264 Macrophage-Like and Smooth Muscles Cells by Bisphosphonates In Vitro. Methods Find Exp. Clin. Pharmacol. 24 (2002), 487 (Abstract only).

* cited by examiner

METHODS FOR TREATING HEART FAILURE USING BISPHOSPHONATE COMPOSITIONS

CROSS-REFERENCE TO RELATED APPLICATIONS

This application is filed under the provisions of 35 U.S.C. § 371 and claims the priority of PCT International Application NO. PCT/US2010/047417, filed on Sep. 1, 2010 and which in turn claims priority to U.S. Provisional Application No. 61/238,797 filed on Sep. 1, 2009, the contents of which are incorporated by reference herein for all purposes.

BACKGROUND OF THE INVENTION

Field of the Invention

The present invention relates to reducing or inhibiting cardiac dysfunction due to heart failure by administering a bisphosphonate compound.

Related Art in the Field

The prevalence of heart failure ("HF") has grown to epidemic proportions as the population ages and as cardiologists have become more successful at reducing mortality from ischemic heart disease, the most common prelude to HF. Specifically, more than 5.7 million Americans suffer from heart failure, and an estimated 550,000 new cases are diagnosed each year (Lloyd-Jones et al. 2009). Despite current treatment options, patients with stage II or III heart failure face a 2-year mortality rate of 25%, poor quality of life, and repeated hospitalizations to manage acute decompensations. The American Heart Association estimates the direct and indirect cost of heart failure in the United States to be $37.2 billion dollars in 2009 alone (Lloyd-Jones et al. 2009).

HF may be caused by many forms of heart disease. Common causes of heart failure include: narrowing of the arteries supplying blood to the heart muscle (coronary heart disease); prior heart attack (myocardial infarction) resulting in scar tissue large enough to interfere with normal function of the heart; high blood pressure; heart valve disease due to past rheumatic fever or an abnormality present at birth; primary disease of the heart muscle itself (cardiomyopathy); and infection of the heart valves and/or muscle itself (endocarditis and/or myocarditis). Each of these disease processes can lead to heart failure by reducing the strength of the heart muscle contraction, by limiting the ability of the heart's pumping chambers to fill with blood due to mechanical problems or impaired diastolic relaxation, or by filling the heart's chambers with too much blood.

Cardiac dysfunction due to cardiotoxicity can also be caused by radiation-induced heart disease (RIHD) and chemotherapeutic agents which are caused by therapeutic interventions to treat malignancies. Cardiotoxicity renders the heart unable to efficiently pump blood throughout the body. Symptoms of this effect include shortness of breath, fatigue, and anemia. These signals indicate that the heart is having difficulty maintaining its essential function. It has also been found that radiation therapy (RT) can cause injury to all the components of the heart, including the damage of small vessels that supply the blood to the heart. It may cause scarring in the heart muscle. Further, the coronary arteries are more prone to clotting after being treated with radiation. The radiation may damage the endothelial lining of the vessels making them form clots more readily. As stated above, the chemotherapeutic agent used in cancer treatment, such as anthracyclines, alkylating agents, antimetabolites, antimicrotubules and etc. can also cause cardiotoxicity.

The dominant pathophysiology associated with HF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy." The counterpoint to systolic dysfunction is diastolic dysfunction, an impairment of the ability to fill the ventricles with blood, which can also result in heart failure even with preserved left ventricular function. Heart failure is ultimately associated with improper function of the cardiac muscle cells involving a decrease in the ability to effectively contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions and the consequent scarring and remodeling results in the development of a dilated and hypocontractile heart.

A more recent finding is that inflammatory cytokines are elevated in patients with heart failure. Indeed, there is a direct relationship between elevated levels of TNF-α and IL-6 and the degree of hemodynamic abnormalities. Similarly, the higher the TNF-α level the more severe the heart failure symptoms. Interestingly, it has been found that TNF-α is not expressed by normal human heart but is expressed in abundant amounts by human failing heart. Furthermore, TNF-α can induce the expression of other inflammatory cytokines.

Numerous compounds are known to be useful for the prevention and treatment of heart failure, including alpha-adrenergic antagonists, angiotensin II antagonists, angiotensin-converting enzyme (ACE) inhibitors, beta-adrenergic antagonists, antihypertensives, calcium channel blockers, diuretics, potassium channel opening vasodilators, renin inhibitors, and serotonin antagonists. However, in view of the high prevalence of heart failure in the general population and the poor prognosis of these patients, there remains a great need for agents that exploit new mechanisms of action and may have better outcomes in terms of relief of symptoms, safety, and patient mortality, both short-term and long-term. New agents may provide a means to achieve better clinical outcomes for those who have or are at risk for heart failure.

SUMMARY OF THE INVENTION

The present invention includes methods and compositions for treating cardiac dysfunctions and diseases related thereto.

In one aspect, the invention includes a method for treating hypertrophy, hypertension, heart failure, ischemic heart disease, ischemia reperfusion injury and acute heart failure of inflammatory etiology, i.e., myocarditis and acute cardiac rejection associated with cardiac transplantation in mammals that includes administering to the mammal a therapeutically effective amount of a bisphosphonate, functional analogue thereof or a pharmaceutically effective salt thereof.

Another aspect of the present invention relates to pharmaceutical compositions comprising a bisphosphonate and a pharmaceutically acceptable carrier or diluent. The bisphosphonate compound may include but is not limited to zoledronic acid, risedronate, alendronate, cimadronate, clodronate, tiludronate, etidronate, ibandronate, piridronate or pamidronate and functional analogues thereof. Preferably the compound is zoledronic acid or ibandronate.

Yet another aspect of the present invention relates to a method for administering to a subject in need thereof an effective amount of a bisphosphonate compound according to the invention and subsequent to the diagnosis of heart failure, the occurrence of a vascular injury, subsequent to a vascular surgical operation or in combination with therapeutic interventions to treat malignancies including radiation therapy and use of anthracycline compounds.

A still further aspect of the present invention relates to use of a bisphosphonate and preferably, zoledronic acid to treat systolic and/or diastolic dysfunction, wherein the zoledronic acid is administered in a therapeutically effective amount to increase the ability of the cardiac muscle cells to contract and relax thereby increasing the filling and emptying of both the right and left ventricle.

A further aspect of the present invention relates to administration of the bisphosphonate compound at least annually, either after the diagnosis of heart failure or after the occurrence of a vascular injury or surgical operation. The amount of the bisphosphonate compound administered is an amount effective to treat or prevent a patient's heart failure. Preferably the effective amount is from about 40 ug/kg to about 125 ug/kg, more preferably from about 50 ug/kg to 100 ug/kg.

Effective treatment can be exhibited by an increase of ejection fraction, increase in diastolic and/or systolic function, improvement in hemodynamics, reduction in inflammatory cytokine levels and neurohormone levels, reduction in markers of inflammation, reduction in injury markers, inhibition of platelet aggregation, improvement in endothelial function, reductions in arrhythmias, and improvement in heart rate variability, improvement in QRS dispersion and QTC prolongation, and improved immune responsiveness, all of which can be tested by skilled artisans with known and available testing regimes.

A still further aspect of the present invention relates to the use of a bisphosphonate compound alone or together with other cardiac therapeutic agents including, but not limited to nitrates, beta-adrenergic blockers, calcium channel antagonists, antihypertensive agents, cholesterol lowering agents, diuretics, ACE inhibitors, non-peptide angiotensin II antagonists, IIb/IIIa antagonists and aspirin in the manufacture of a medicament for the prevention of cardiovascular events, for example stroke, heart failure, cardiovascular death, myocardial infarction, worsening of angina, cardiac arrest, or need for revascularization procedures.

Another aspect of the present invention relates to a method of treating cardiovascular diseases and diseases related thereto, wherein a subject is administered Vitamin D (cholecalciferol or egrocalciferol) in dosages ranging from about 50,000-125,000 IU in a single or multiple dosages and a subsequent administration of a bisphosphonate in an effective amount to treat or prevent heart failure in the subject.

Yet another aspect of the present invention relates to a method of delivering a bisphosphonate compound in a local or targeted fashion using interventional techniques. This could be accomplished by direct coronary injection in multiple clinical contexts. In one preferred embodiment, the bisphosphonate could be directly infused into a coronary artery of a patient undergoing an emergency intervention for reperfusion during acute myocardial infarction (AMI). In this scenario, direct intracoronary infusion of the bisphosphonate compound may have a significant effect on inflammation associated with reperfusion and healing or reperfusion injury, on infarct size, on development of sequelae such as heart failure, or on clinical outcomes. In an alternative embodiment, the bisphosphonate compound could be injected into all coronary arteries (for example via the left main and right coronary arteries) after heart transplantation. It is anticipated that timing, dosage, and dosage intervals would be determined based on the disease the bisphosphonate is intended to treat or prevent, as well as the clinical context in which the bisphosphonate is administered.

Additional aspects of the present invention which may be used with local or targeted drug delivery methods include coupling of the bisphosphonate compound to a carrier such as a nanoparticle, microsphere, or another type of particle of appropriate size, shape, and other characteristics to effect targeted, local delivery of the therapy. Associated devices or delivery vehicles are preferably designed for intravascular or intracardiac placement. These methods may include those in which devices or delivery vehicles are designed to promote delivery of the bisphosphonate compound over time. Such methods may include but are not limited to intravascular or intracardiac prostheses that are coupled to or constructed entirely out of bioabsorbable polymer. Alternatively, the bisphosphonate could be eluted from another material that may be durable or bioabsorbable.

In another aspect, the bisphosphonate compound may be released over time through a membrane or other barrier from a patch residing in the heart or the vasculature. Further, the bisphosphonate compound may be delivered by elution from vascular paving or hydrogel, including by way of deployment of a hydrogel-coated or other drug-eluting balloon.

In a further aspect, the present invention provides for a method wherein the bisphosphonate compound may be combined with a device that is currently used to treat cardiovascular disorders. For example, the bisphosphonate compound could be eluted, in combination with an anti-restenosis drug or alone, from a drug-eluting stent placed in the treatment of acute myocardial infarction (AMI).

In a still further aspect, the present invention provides administering a bisphosphonate, preferably zoledronic acid, in combination with therapeutic interventions to treat malignancies, wherein such interventions include radiation therapy and/or the use of an antineoplastic agent used in chemotherapy.

A final aspect of the present invention relates to a kit for treatment or prevention of heart failure and negative side-effects thereof, the kit comprising at least one dose of a bisphosphonate in an therapeutically effective amount to treat or prevent the symptoms of heart failure. The kit may optionally include a sufficient daily dosage of Vitamin D for consumption from 7 days to one month.

Other aspects, objects, features and advantages of the present invention would be apparent to one of ordinary skill in the art from the following detailed description illustrating the preferred embodiments of the invention.

DETAILED DESCRIPTION OF THE INVENTION

The present invention is directed to compositions and methods for treatment of heart failure including treating any one or more of the conditions underlying heart failure, including, without limitation, decreased cardiac contractility, abnormal diastolic or systolic compliance, reduced stroke volume, pulmonary congestion, and decreased cardiac output, while minimizing or attenuating deleterious effects commonly associated with previously used compounds.

Bisphosphonates, a class of compounds that are pyrophosphate analogues, have been used for thirty (30) years to treat skeletal disorders caused by increased osteoclastic bone resorption (Rosen, 2005). The first compound approved for use in treating Paget's disease of bone was etidronate. This was followed by more potent nitrogen-containing bisphosphonates: alendronate, risedronate and ibandronate; that have become the first line of therapy for postmenopausal osteoporosis. However, until recently, these agents had to be administered orally, requiring weekly to monthly dosing. Now two bisphosphonates: ibandronate and zoledronic acid, are efficacious in the treatment of osteoporosis when administered intravenously, either quarterly each year (ibandronate), or annually (zoledronic acid).

Bisphosphonates are the current drug of choice for osteoporosis because they reduce fracture rates as well as the attendant disability (Rosen, 2005). Although two types of osteoporotic fractures (vertebral and hip) are associated with increased mortality, until recently no clinical trial using bisphosphonates to treat this disease has shown a reduction in mortality. Recently, a clinical study was conducted wherein patients who were within 90 days of surgical repair of a hip fracture were randomized to receive either zoledronic acid or placebo at baseline and yearly thereafter, with the primary response variable being the rate of new clinical fractures (Colon-Emeric et al. 2004). The trial had a positive outcome with a 35% reduction in the risk of all clinical fractures (Lyles et al. 2007). Further, a 28% reduction in mortality was observed in those patients who received zoledronic acid compared to the placebo subjects.

Another study of interest described the use of genetically engineered mice exhibiting the effects of having Hutchinson-Gilford Progeria Syndrome (HGPS). The people diagnosed with this disease usually have small, fragile bodies, like those of elderly people. Later, the condition causes wrinkled skin, atherosclerosis and cardiovascular problems. The mice were treated with pravastatin and zoledronic acid in an attempt to slow premature aging, growth retardation, vascular disease, hair loss, and osteoporosis. (Varela 2008) In combination, these therapies were reported to increase the median lifespan from 101 to 179 days.

Upon seeing the results of these studies, it was theorized by the present inventors that the bisphosphonate could be responsible for the reduction in mortality. Specifically, this hypothesis was based on epidemiologic evidence linking cardiovascular disease and osteoporosis, and overlapping patterns of elevated inflammatory cytokines associated with disability and death in both hip fracture patients and heart failure patients. The testing results, as discussed herein, provide evidence that administration of the bisphosphonate can positively impact a mammal in heart failure.

DEFINITIONS

The term "bisphosphonate," as used herein, means any compound which is an analog of endogenous pyrophosphate whereby the central oxygen is replaced by carbon. Bisphosphonates include aminobisphosphonates. Bisphosphonates include, but are not limited to the following compounds: zoledronic acid, risedronate, alendronate, cimadronate, clodronate, tiludronate, etidronate, ibandronate, piridronate, or pamidronate and functional analogues thereof.

The term "zoledronic acid," as used herein, means to include the free acid itself, i.e., 1-hydroxy-2-(imidazol-1-yl)ethane-1,1-diphosphonic acid, as well as any pharmaceutically acceptable salts and hydrates thereof and solvates thereof formed from other solvents used for its crystallization. 1-hydroxy-2-(imidazol-1-yl)ethane-1,1-diphosphonic acid and its pharmacologically acceptable salts, hydrates and solvates are well-known from the literature. They can be prepared by procedures known in the art, such as described, e.g., in U.S. Pat. No. 4,939,130. See also U.S. Pat. Nos. 4,777,163 and 4,687,767. The contents of the latter three patents are hereby incorporated by reference in their entirety.

The term "heart failure," as used herein, means impaired cardiac function that renders the heart unable to maintain the normal blood output at rest or with exercise, or to maintain a normal cardiac output in the setting of normal cardiac filling pressure. A left ventricular ejection fraction of about 40% or less is indicative of heart failure (by way of comparison, an ejection fraction of about 55% to 60% percent is normal). Patients with heart failure display well-known clinical symptoms and signs, such as tachypnea, pleural effusions, fatigue at rest or with exercise, contractile dysfunction, and edema. Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

The term, "ischemic heart disease," as used herein, means any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

The term "atherosclerotic cardiovascular disease," as used herein, means a cardiovascular disease that is associated with or secondary to an atherosclerotic condition, e.g. a diseased state of the arteries characterized by an accumulation of intimal smooth muscle cells, accumulation of macrophages and T-lymphocytes, formation of large amounts of connective tissue matrix, and accumulation of lipid, primarily in the form of cholesterol or cholesterol esters within the cells and the surrounding connective tissue, and accumulation of necrotic debris.

The term "myocardial infarction," as used herein, means a process by which ischemic disease results in a region of the myocardium being replaced by scar tissue.

The term "cardiotoxic compound," as used herein, means chemotherapeutic agents including but not limited to anthracyclines, such as, Doxorubicin, Daunorubicin, Epirubicin, Idarubicin, and Mitoxantrone; alkylating agents, such as, Vusulfan, Cisplatin, Cyclophosphamide, Ifosfamide and Mitomycin; Antimetabolites, such as, Capecitabine, Cytarabine and Fluorouracil; Antimicrotubules, such as, Paclitazel and Vinca alkaloids; Biological agents, such as, Alemtazumab, Bevacizumab, Cetuximab, Rituximab, Trastuzumab, IL-2 and Interferon-α; and miscellaneous, such as, Imatnib, Arsenic trioxide and Etoposide.

The term "hypertension," as used herein, means blood pressure that is considered by a medical professional (e.g., a physician or a nurse) to be higher than normal and to carry an increased risk for developing congestive heart failure.

The term "treating," as used herein, means that the administration of a bisphosphonate compound slows or inhibits the progression of heart failure during the treatment, relative to the disease progression that would occur in the absence of treatment, in a statistically significant manner. Well known indicia such as left ventricular ejection fraction, exercise performance, and other clinical tests as enumerated above, as well as survival rates and hospitalization rates, event rates or composite endpoints may be used to assess disease progression. Whether or not a treatment slows or prevents disease progression in a statistically significant manner may be determined by methods that are well known in the art.

The term "preventing," as used herein, means minimizing or partially or completely inhibiting the development of heart failure in a mammal at risk for developing congestive heart failure. Determination of whether heart failure is minimized or prevented by administration of a bisphosphonate is made by known methods.

The term "at risk for heart failure", as used herein, means an individual who smokes, is obese (i.e., 20% or more over their ideal weight), has (or had) high blood pressure, ischemic heart disease, a myocardial infarct, a genetic defect known to increase the risk of heart failure, a family history of heart failure, myocardial hypertrophy, hypertrophic cardiomyopathy, left ventricular systolic dysfunction, coronary bypass surgery, vascular disease, atherosclerosis, alcoholism, periocarditis, a viral infection, gingivitis, an eating disorder (e.g., anorexia nervosa or bulimia), is an alcoholic or cocaine addict, and/or has been treated with radiation therapy or chemotherapy for treat malignancies.

The term "therapeutically effective amount," as used herein, means an amount of a compound or combination of compounds that ameliorates, attenuates, or eliminates one or more symptoms of heart failure or prevents or delays the onset of one or more symptoms of heart failure as defined herein.

The term "pharmaceutically acceptable," as used herein, means that the carrier, diluent, excipients, and/or salt must be compatible with the other ingredients of the formulation, and not deleterious to the patient. Examples of pharmaceutically acceptable salts of the compounds include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4{}^+$, or $NR'_4{}^+$ (wherein R' is for example a $C_{1-4}$ alkyl group).

The term "a form of Vitamin D," as used herein, means any from of Vitamin D and functionally active analogue including Vitamin D2 (ergocalciferol or calciferol) and Vitamin D3 (cholecalciferol); hormones including calcidiol, dihydrotachysterol and calcitriol; Vitamin D analogues or metabolites including doxercalciferol and paricalcitol.

The term "functionally active analog," as used herein, means compounds derived from a particular parent compound by straightforward substitutions that do not result in a substantial (i.e. more than 100×) loss in the biological activity of the parent compound, where such substitutions are modifications well-known to those skilled in the art, e.g., esterification, replacement of hydrogen by halogen, replacement of alkoxy by alkyl, replacement of alkyl by alkoxy, etc.

As used herein, the term "heart tissue" includes, without limitation, the myocardium of the heart (including cardiac muscle fibers, connective tissue (endomysium), nerve fibers, capillaries, and lymphatics); the endocardium of the heart (including endothelium, connective tissue, and fat cells); the epicardium of the heart (including fibroelastic connective tissue, blood vessels, lymphatics, nerve fibers, fat tissue, and a mesothelial membrane consisting of squamous epithelial cells); and any additional connective tissue (including the pericardium), blood vessels, lymphatics, fat cells, progenitor cells (e.g., side-population progenitor cells), and nervous tissue found in the heart.

The bisphosphonate, and specifically zoledronic acid, is preferably used in the form of pharmaceutical compositions that contain a therapeutically effective amount of the bisphosphonate active ingredient optionally together with or in admixture with inorganic or organic, solid or liquid, pharmaceutically acceptable carriers which are suitable for administration.

The pharmaceutical compositions may be, for example, compositions for enteral, such as oral, rectal, aerosol inhalation or nasal administration, compositions for parenteral, such as intravenous or subcutaneous administration, or compositions for transdermal administration, e.g., passive or iontophoretic. Preferably, the pharmaceutical compositions are for intravenous administration. The pharmaceutical compositions may also be for direct intracoronary injection or elution from an intravascular or intracardiac device.

The particular mode of administration and the dosage may be selected by the attending physician taking into account the particulars of the patient, especially age, weight, life style, activity level, hormonal status, e.g., post-menopausal, and bone mineral density as appropriate. Most preferably, however, zoledronic acid is administered intravenously and the dosage of the zoledronic acid may depend on various factors, including sex, age, weight and/or individual condition of the subject.

Normally the dosage is such that a single dose of a bisphosphonate, such as zoledronic acid or salt or hydrate thereof is from about 0.002 to about 20.0 mg/kg, preferably from 0.01 to 1 mg/kg, and more preferably from about 0.04 mg/kg to about 0.125 mg/kg. The term "mg/kg" means mg of drug per kg body weight of the subject. The dosage will be determined to correspond with the frequency of administering the compound.

In accordance with the present invention, the bisphosphonate, and preferably zoledronic acid or ibandronate, is dosed at intervals of at least about once a month, every three months, six months, e.g., once every 180 days, or less frequently, conveniently once a year, or at any interval in between, e.g., once every 7, 8, 9, 10 or 11 months. The dose mentioned above, either administered as a single dose (which is preferred) or in several partial doses, is preferably administered once per year (understanding, of course, that it may not be exactly one year to date but rather at yearly check-ups).

Timing and location for direct intracoronary injection or targeted intravascular or intracardiac delivery of the bisphosphonate compound may depend on the disorder being treated. In one preferred embodiment, bisphosphonate treatment during an acute myocardial infarction (AMI) would preferably include at least one acute direct injection into the coronary supplying the jeopardized myocardium at the time of interventional reperfusion. In an alternative embodiment, bisphosphonate treatment after heart transplant may include direct injection into all coronary arteries after cardiac transplantation and periodically thereafter. Such patients are frequently catheterized for biopsies and other diagnostic or therapeutic procedures; these catheterizations may provide a natural opportunity for targeted delivery of bisphosphonate therapy in these disorders. In another alternative embodiment, bisphosphonate treatment of myocarditis may be performed by intracoronary injection at the time of diagnosis and periodically thereafter. In yet another alternative embodiment, bisphosphonate therapy for cardiomyopathy and various causes of HF may be administered as either a single (one-time) or periodic treatment.

Formulations in single dose unit form contain preferably from about 1% to about 90%, and formulations not in single dose unit form contain preferably from about 0.1% to about 20%, of the zoledronic acid active ingredient. Pharmaceutical preparations for enteral and parenteral administration are, for example, those in dosage unit forms, such as drages, tablets or capsules and also ampoules. They are prepared in a manner known per se, for example, by means of conventional mixing, granulating, confectioning, dissolving or lyophilizing processes.

For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or drage cores. Suitable carriers are especially fillers, such as sugars, for example, lactose, saccharose, mannitol or sorbitol, cellulose preparations and/or calcium phosphates, for example, tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof, such as sodium alginate. Adjuncts are especially flow-regulating agents and lubricants, for example, silicic acid, talc, stearic acid or salts thereof, such as magnesium or calcium stearate, and/or polyethylene glycol. Drage cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Coloring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticizer, such as glycerol or sorbitol. The dry-filled capsules may contain the active ingredient in the form of a granulate, for example, in admixture with fillers, such as lactose; binders, such as starches; and/or glidants, such as talc or magnesium stearate, and, where appropriate, stabilizers. In soft capsules, the active ingredient is preferably dissolved or suspended in suitable liquids, such as fatty oils, paraffin oil or liquid polyethylene glycols, it being possible also for stabilizers to be added.

Parenteral formulations are especially injectable fluids that are effective in various manners, such as intra-arterially, intramuscularly, intraperitoneally, intranasally, intradermally, subcutaneously or preferably intravenously. Such fluids are preferably isotonic aqueous solutions or suspensions which can be prepared before use, for example, from lyophilized preparations which contain the active ingredient alone or together with a pharmaceutically acceptable carrier. The pharmaceutical preparations may be sterilized and/or contain adjuncts, for example preservatives, stabilizers, wetting agents and/or emulsifiers, solubilizers, salts for regulating the osmotic pressure and/or buffers.

Suitable formulations for transdermal application include an effective amount of the zoledronic acid active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

In another embodiment, the present invention relates to ensuring that the subject has an adequate level of Vitamin D before the administration of the bisphosphonate compound and specifically zoledronic acid. The level of Vitamin D can be easy determined by a simple blood test that determines the level of Calcidiol (25-hydroxyvitamin D). The unit dose of Vitamin D will be determined by the specific form, the number of day of administration, age and condition of patient, and level of determined Vitamin D deficiency. For example, cholecalciferol may in a unit tablet dose of from about 400 to 5000 IU or in intramuscular form from about 50,000 units/cc to 100,000 units/cc; egocalciferol in unit capsule dose of from about 400 to 50,000 IU; oral calcitriol in a dose from about 0.10 to about 1 mcg which can be administered at least once a day or in multiple administrations; calcidiol or doxercalciferol, both of which are vitamin D analogues may be administered in dose units of from about 300 to 2000 IU.

In yet another embodiment, the present invention relates to a formulation that includes zoledronic acid, a form of Vitamin D and optionally calcium in an essentially homogeneous mixture, wherein a solution or solid unit dose can be administered in a single dose. The single dose can be administered daily, monthly or yearly, or at some intermediate interval depending on the bisphosphonate compound.

In some applications, it may be advantageous to utilize the active agent in a "vectorized" form, such as by encapsulation of the bisphosphonate active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

EXAMPLES

Material and Methods
Bisphosphonate Compound
Zoledronic acid (Zometa®, Reclast®) bone density conservation agent IUPAC: (1-hydroxy-2-imidazol-1-yl-1-phosphoethyl)phosphonic acid MF: $C_5H_{10}N_2O_7P_2$/Entrez PCompound CID: 68740

Zoledronic acid is FDA approved for the treatment of postmenopausal osteoporosis, Paget's Disease of bone, and for the prevention of skeletal complications in patients with certain cancers such as multiple myeloma and prostate cancer.

Testing Animals

Gottingen miniswine were obtained from Marshall BioResources in New York. The miniswine heart failure model created by Synecor (N'diaye, 2008) manifests numerous sequelae of heart failure seen in humans including significant systolic dysfunction, reduced cardiac output, and LV dilatation and hypertrophy. Miniswine is an ideal subspecies in which to create this model of heart failure for numerous reasons. The coronary artery anatomy and distribution in miniswine are remarkably similar to those in humans, as are their heart-to-body size and weight ratios. Porcine and human hearts have only a sparse collateral network, an essential quality when seeking to reproduce the overall physiologic profile and clinical syndrome associated with HF. The swine subject facilitates the creation of a consistent and reproducible model. Miniswine in particular were selected for their smaller size at sexual maturity, ease in handling, and docile nature. Furthermore, the Gottingen miniswine have been extensively used to model human metabolic bone disease, especially osteoporosis.

All animal husbandry was done in accordance to *The Guide for the Care and Use of Laboratory Animals* published by the Institute of Laboratory Animal Resources Commission on Life Science National Research Council, NATIONAL ACADEMY PRESS, 1996, and applicable USDA regulations without exception. Animals were housed on site for a minimum of 1 week prior to study assignment. Appropriate SOPs and protocols were followed for housing conditions, health status review, diet, pre-op instructions, and post operative care. All animals remained on site for the duration of the study. Prior to transport, the animals were inspected by the veterinarian and cleared for transport and for use in the research study. The animals were transported in a climate controlled truck and have access to water at all times. During transport the animals were checked every four hours to assure their safety and ensure that water was available. All Synecor animals were identified by a unique number which was either tattooed in ear or by ear tag.

Description of Experimental Design and Identification of Animal Procedures.

Experimental Design: The miniswine underwent sequential coronary embolization procedures to induce irreversible heart failure. Two to four weeks before the study, each animal was given 20,000 to 40,000 IU of cholecalciferol orally. Sequential coronary embolization procedures were performed on each animal in the manner described in IACUC Protocol No. 014-12-06 until EF≤35% or at least 20% less than the original reading. Specifically, each animal underwent sequential cardiac catheterizations for embolization of the LAD with gelatin sponge particles. All interventional procedures were performed using sterile technique under general anesthesia with adequate post-operative pain control. Embolization procedures were performed every 1-2 weeks until EF (measured pre-embolization)≤35% or at least 20% less than the original reading. This technique eventually exhausted the ability of the myocardium to compensate for ischemic injury, leading to HF characterized by decreased ejection fraction, increased SVR, LV hypertrophy and increased LV end-diastolic volume, increased PCWP, increased ANF and norepinephrine secretion, and patchy myocardial fibrosis on histologic examination (Sabbah et al. 1991, Sakaguchi et al. 2003, Li et al. 2005).

After a 2 week stabilization period followed by documentation of persistent HF by cardiac catheterization, animals were randomly assigned to a standard dose drug group or control group. Baseline studies in addition to the echocardiogram included 24 hr Holter monitoring and measurement of serum, plasma, and cellular biomarkers. The animals were treated with the study drug or placebo 24 hours after acquisition of the baseline studies. Over the next 12 weeks the miniswine were maintained as described below and studies were performed at intervals as summarized in Table 1.

| Procedure | Baseline - Documented HF (Day 1) | 24 Hrs (Day 2) | 1 Week (Day 7) | 2 Weeks (Day 14) | 6 Weeks (Day 42) | 12 Weeks (Day 84) |
|---|---|---|---|---|---|---|
| Echocardiogram | X | | | X | X | X |
| 24 Hour Holter | X (0-24 hrs) | X (24-48 hrs post-drug) | X | X | X | X (24 hrs prior to endpoint study) |
| Blood Draw/Markers | X | X | X | X | X | X |
| Study Drug Infusion 15 min infusion | | X | | | | |

Study Drug: zoledronic acid (bone density conservation agent) to be administered as follows:
a. Group 1 (Control) animals received a 15-30 cc saline placebo infusion.
b. Group 2 (Standard Dose) animals received an intravenous infusion of 100 microgram/kilogram body weight of zoledronic acid in 15 cc of 0.5 normal saline over 15 minutes.

Interventional Procedures:

Coronary Embolization: Each animal underwent ≥2 cardiac catheterizations for embolization of the LAD with gelatin sponge particles. Embolization procedures were performed every 2 weeks until EF (measured pre-embolization) <35% or at least 20% less then the original reading. A 20 mg piece of gelatin sponge (Gelfoam; Pharmacia & Upjohn, Peapack, N.J.) was cut into 1 $mm^3$ pieces) and mixed with 2 ml contrast media and 2 ml heparinized saline. 1.0 ml of the gelatin-sponge mixture was injected over 90 seconds into the LAD between the first and second diagonal branches. Embolization was repeated every 30 minutes until significant impairment of LAD fill time or malignant arrhythmia occurs. Bretylium tosylate (5 mg/kg) was administered prior to embolization to reduce the risk of arrhythmia. (Schumann 1993). EKG was monitored continuously throughout the procedure.

Hemodynamic Assessment: The hemodynamic assessments described here were performed during each interventional procedure. Aortic and LV end-diastolic pressures were measured at baseline, throughout, and up to 1 hour after each microembolization procedure via catheter-tip micromanometers (Millar Instruments, Houston, Tex.). PCWP, PA, RA, and RV pressures were measured during the same timeframe using a Swan-Ganz catheter with coupled pressure transducer. Triplicate cardiac output measurements were performed using the thermodilution technique. Arterial pressure was measured continuously via the femoral arterial sheath.

Coronary Angiography: Cineangiography and ventriculography was performed before and after each embolization procedure to assess LV volumes and LAD fill time.

Continuous Holter Monitoring was performed for 24 hrs pre- and post-drug infusion, and also for 24 hrs each at 1 week, 2 weeks, 6 weeks, and 12 weeks.

Biomarkers: The following biomarkers were assessed at baseline, 24 hrs, 1 week, 2 weeks, 6 weeks, and 12 weeks: CRP, IL6, IL-1, IL-18, BNP, TNF alpha, ESR, osteoprotogerin, cardiac specific troponins, dendritic cell proliferation assay (flow cytometry), gamma-delta T cell assay (flow cytometry), granzyme release (measuring activity of CD8 lymphocytes), interferon gamma assay (activity of CD4 lymphocytes/Th1 helper response), quantative immunoglobulin levels (B cell function), 25-hydroxyvitamin D, PTH, CTX-1, CTX-2, P1NP, and osteocalcin. Alternatively or in addition, blood was banked at these time points for analysis at a later date.

Necropsy and histology was performed after each animal is euthanized under anesthesia at 12 weeks. Animals initiate the study 3 at a time, staggered at 6 week intervals.

Example 1

The utility of the a bisphosphonate compound of the present invention as medical agents in the treatment or prevention of HF in animals, particularly mammals (e.g. humans) was demonstrated by the activity of the compounds in in vivo testing described below.

This example describes the treatment of a miniswine for induced heart failure. Approximately 1 week before the procedure to create heart failure, the swine was given 10-15,000 IU of cholecalciferol orally. The miniswine underwent sequential coronary embolizations to create heart failure in the manner described above. Catheterizations were performed under general anesthesia and the microembolization procedures were discontinued when ejection fraction (EF) was approximately ≥20% relative to the initial testing baseline.

After the swine developed heart failure as evidenced by the reduction in EF value, the swine was then treated with zoledronic acid. Swine 1 (2514), 2 (4997) 3 (5272) and 4 (6928) received an intravenous infusion of 100 microgram/kilogram body weight of zoledronic acid in 15 cc of 0.5 normal saline over 15 minutes. Swine 5 (6167), 6 (7479), 7 (5760) and 8 (0492) received a 15 cc saline placebo infusion.

Figure 1:
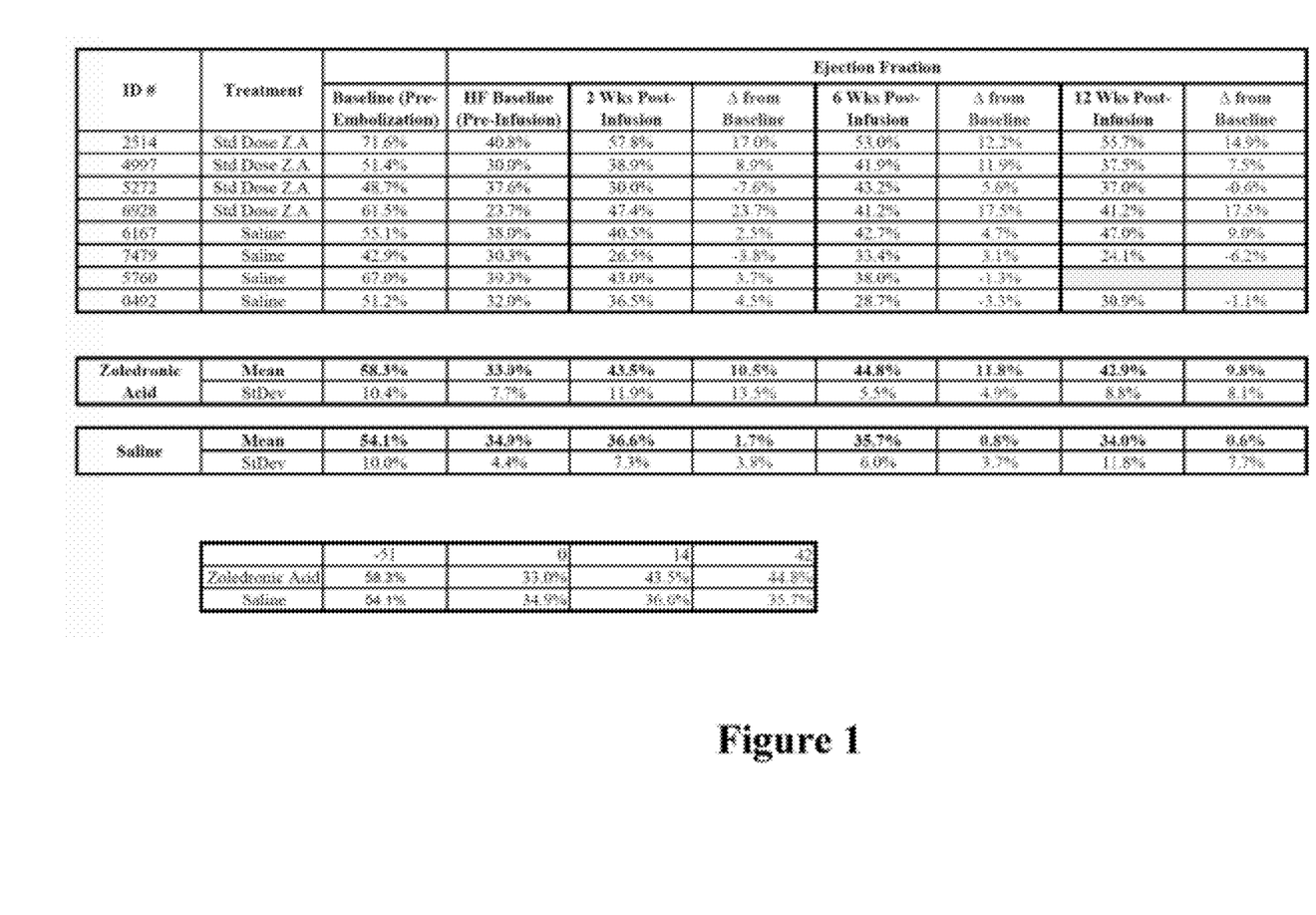
FIG. 1 shows the compilation of the results of test swine over the testing period.

After the administration of the drug and placebo, the EF was tested approximately every 2 weeks. The results for both the control and zoledronic acid group are shown in FIG. 1. As evidenced by the results set forth in FIG. 1, the swine 2514 had an ejection fraction at baseline that was at least 70% and during the series of embolizations, the swine 2514 had a reduction to 40% (a value consistent with heart failure). Notably on day 42, swine 2514 was embolized for a final time that effected the reduction to 40% EF. 100 ug/kg of zoledronic acid was then administered in this test animal (2514) and 14 days after the zoledronic acid was administered to the test animal, the ejection fraction had increased almost to 57.8% which was held for approximately 12 weeks. Test swine 2, 3 and 4, also exhibited an increase in EF. Notably, the control swine did not exhibit an increase in the ejection fraction and stay at essentially the same level of ejection fraction after completion of embolization.

Figure 2:
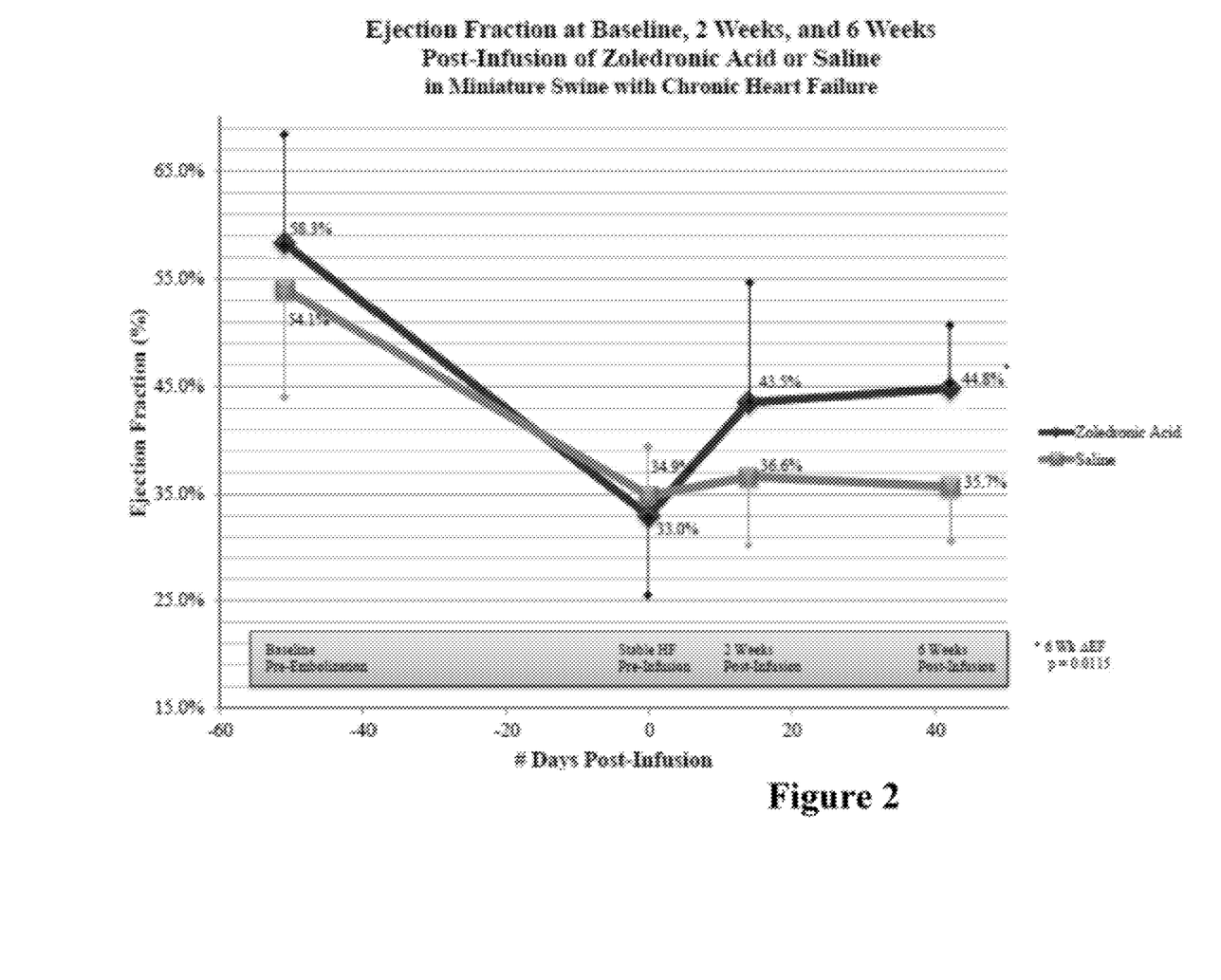
FIG. 2 is a graph showing the average values of testing swine administered the zoledronic acid or placebo.

FIG. 2 graphically illustrates the average values of the control and zoledronic treated swine as set forth in FIG. 1 and it is evident that after treatment with zoledronic acid, the ejection fraction slowly increased over the six week period. Notably the effect was statically significant. The control group did not see a similar effect. This result indicates that the zoledronic acid compound reduced the effects of heart failure.

Figure 3:
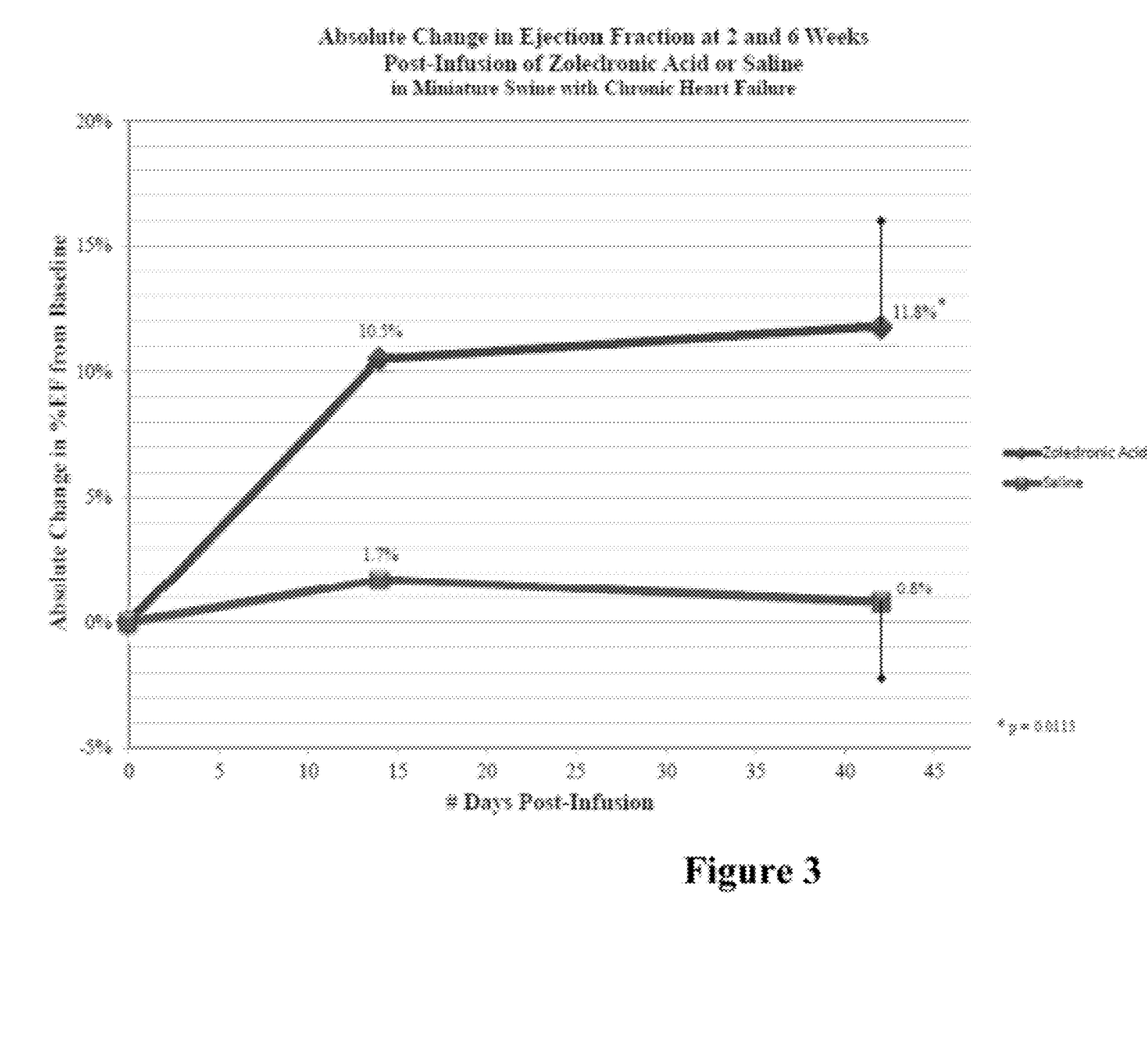
FIG. 3 is a graph showing the absolute value of the increase of ejection fraction

FIG. 3 graphically illustrates that at the end of six weeks there was almost a 12% increase in the ejection fraction, which is time-dependent and statistically significant. In the control the increase in the control group of swine showed approximately a 1% increase. Based on the above data, it may be concluded that treatment with a bisphosphonate is effective and can be proposed as a therapy for improvement of cardiac function in a variety of disease states, including HF.

Although the invention has been described with reference to specific preferred embodiments, it will be appreciated that many variations may be made to the invention without departing from the spirit or scope thereof. All such modifications are intended to be included within the scope of the following claims.

REFERENCES

All references cited herein are hereby incorporated by reference herein for all purposes.

Colon-Emeric C, Caminis J, Suh T T, Pieper C F, Janning C, Magaziner J, Adachi J, Rosario-Jansen T, Mesenbrink P, Horowitz Z D, Lyles K W The HORIZON Recurent Fracture Trial: Design of a clinical trial in the prevention of subsequestn fractures in elders after low trauma hip fracture repair. *Curr Med Opin Res.,* 2004; 20:903-910.

N'diaye C S, O'Connor C M. Progressive myocardial dysfunction induced in porcine model by two-stage coronary embolization with gelatin sponge. Poster presented at Alpha Omega Alpha Research Symposium Duke University Medical Center, Aug. 8, 2008.

Li H H, Shen Z Y, Hui J, Li K, Zheng L, Jiao P, Teng X M, Zhu J Z, Gao W D, Yang J H, Zhou B Y. 2005. A pig model of myocardial infarction by intracoronary embolization with gelatin sponge [abstract in English; article in Chinese]. *Zhonghua Yi Xue Za Zh,* 85(9):599-601.

Lloyd-Jones D, Adams R, Carnethon M, et al. Heart Disease and Stroke Statistics—2009 Update: A Report From the American Heart Association Statistics Committee and Stroke Statistics Subcommittee. *Circulatio,* Jan. 27, 2009 2009; 119(3):e21-181.

Lyles K W, Colon-Emeric C S, Magaziner J S, Adachi J D, Pieper C F, Mautalen C, Hylstrup L, Recknor C, Nordsletten L, Moore K A, Lavecchia C, Zhang J, Mesenbrink P, Hodgson P K, Abrams K, Orloff J J, Horowitz Z, Eriksen E F, Boonen S. Zoledronic acid and clinical Fractures and Mortality after Hip Fracture. *N Engl J Med.,* 2007; 357: 1799-1809.

Reinwald S, Burr D. Review of Nonprimate Large Animal Models for Osteoporosis Research. *J Bone Miner Res* 2008 23:1353-13468.

Rosen, C J. Postmenopausal Osteoporosis. *N Engl J Med.,* 2005 353:595-603.

Sabbah H N, Stern P D, Kono T, Gheorgiade M, Levine T B, Jafri S, Hawkins E T, Goldstein S. A canine model of chronic heart failure produced by multiple sequential microembolizations. *Am J Physiol Heart Circ Physio.,* 1991; 260(4):H1379-84.

Sakaguchi G, Sakakibara Y, Tambara K, Lu F, Premaratne G, Nishimura K, Komeda M. 2003. A pig model of chronic heart failure by intracoronary embolization with gelatin sponge. *Ann Thorac Surg.,* 75:1942-7.

Schumann R E, Harold M E, Gillette P C, Swindle M M, Gaymes C H. Prophylactic treatment of miniswine with bretylium for experimental cardiac catheterization. *Lab Anim Sci.,* 1993 June; 43(3):244-6.

Swindle, M M. Technical bulletin: anesthesia and analgesia in mimiswine http://www.sinclairresearch.com/PDF Files/anesthesia and analgesia in miniswine.pdf Swindle M M, Horneffer P J, Gardner T J, Gott V L, Hall T S, Stuart R S, Baumgartner W A, Borkon A M, Galloway E, Reitz B A. Anatomic and anesthetic considerations in experimental cardiopulmonary surgery in miniswine. *Lab Anim Sci.,* 1986 August; 36(4):357-61.

Varela I, Pereira S, Ugalde A P, Navarro C L, Suarez M F, Cau P, Cadinanos J, Osorio F G, Foray N, Cobo J, de Carlos F, Levy N, Freije J M P, Lopez-Otin C. Combined treatment with statins and aminobisphosphonates extends longevity in a mouse model of human premature aging. *Nature Medicine,* 2008; 14:767-772.

That which is claimed is:

1. A method of treating cardiac dysfunctions due to heart failure in a subject experiencing decreased ejection fraction, said method comprising: administering to said subject a dosage of a bisphosphonate or a pharmaceutically effective salt thereof, wherein the bisphosphonate is zoledronic acid, wherein the dosage is in a therapeutic amount from about 40 ug/kg to about 125 ug/kg to provide an increase in the ejection fraction in the subject after administration of the bisphosphonate.

2. The method of claim 1, wherein the dosage is annually administered to the subject.

3. The method of claim 1, wherein the subject exhibits an increase in ejection fraction of from about 10% to 20% after administration of the zoledronic acid.

4. The method of claim 1, wherein the zoledronic acid is administered after a dosage of Vitamin D.

5. The method of claim 1, wherein the dosage is semi-annually administered to the subject.

6. The method of claim 1, wherein the heart failure is due to decrease of contraction of the left ventricle.

7. The method of claim 1, wherein the heart failure is due to an increase in inflammatory cytokines.

8. The method of claim 1, further comprising administering to the patient at least one other therapeutic agent selected from the group consisting of nitrates, beta-adrenergic blockers, angiotensin converting enzyme inhibitors, calcium channel antagonists, antihypertensive agents, cholesterol lowering agents, diuretics, ACE inhibitors, cardiac glycosides, non-peptide angiotensin II antagonists, IIb/IIIa antagonists and aspirin.

9. The method of claim 1, wherein said heart failure results from hypertension; ischemic heart disease; exposure to a cardiotoxic compound; radiation therapy, myocarditis; thyroid disease; viral infection; drug abuse; alcohol abuse; periocarditis; atherosclerosis; vascular disease; hypertrophic cardiomyopathy; acute myocardial infarction; ventricular systolic dysfunction; ventricular diastolic dysfunction, coronary bypass surgery; or a genetic defect.

10. The method of claim 1, wherein the subject has undergone a myocardial infarction.

11. The method of claim 1, wherein the bisphosphonate is administered after the diagnosis of heart failure in the subject.

12. The method of claim 2, wherein the bisphosphonate is administered intravenously.

13. The method of claim 9, wherein the bisphosphonate is administered simultaneously with a cardiotoxic compound or radiation therapy.

14. The method of claim 1, wherein the subject experiences improved cardiac ejection fraction, and/or increased cardiac output after administration of the bisphosphonate.

15. The method of claim 14 wherein the dosage of the zoledronic acid is about 100 ug/kg.

16. The method of claim 1, wherein the dosage is administered annually or semi-annually to the subject.

17. The method of claim 15, wherein the zoledronic acid is administered after a dosage of Vitamin D.

18. The method of claim 17, wherein the bisphosphonate is administered intravenously.

19. A method of increasing ejection fraction in a subject experiencing such cardiac dysfunctions, said method comprising: administering to said subject a dosage of zoledronic acid or a pharmaceutically effective salt thereof, wherein the dosage is in a therapeutic amount from about 40 ug/kg to about 125 ug/kg to increase ejection fraction from about 10 to about 20% in the subject.

\* \* \* \* \*